(12) United States Patent
Yuki et al.

(10) Patent No.: US 6,994,283 B1
(45) Date of Patent: Feb. 7, 2006

(54) METHOD FOR PULVERIZING TO FINE POWDER

(75) Inventors: Tetuo Yuki, Kyoto (JP); Shuji Watanabe, Shiga (JP)

(73) Assignee: Nippon Shinyaku Co., Ltd., (JP)

( * ) Notice: Subject to any disclaimer, the term of this patent is extended or adjusted under 35 U.S.C. 154(b) by 0 days.

(21) Appl. No.: 10/069,192

(22) PCT Filed: Apr. 21, 2000

(86) PCT No.: PCT/JP00/02616

§ 371 (c)(1),
(2), (4) Date: Oct. 23, 2001

(87) PCT Pub. No.: WO00/64875

PCT Pub. Date: Nov. 2, 2000

(30) Foreign Application Priority Data

Apr. 23, 1999 (JP) .................................. 11/116810

(51) Int. Cl.
*B02C 19/12* (2006.01)
(52) U.S. Cl. .......................................... 241/5; 241/27
(58) Field of Classification Search ................. 514/357; 241/30, 5, 27
See application file for complete search history.

(56) References Cited

U.S. PATENT DOCUMENTS 5,972,976 A * 10/1999 Hidaka et al. ............... 514/357

OTHER PUBLICATIONS

Matsunaga Y et al: "Effects of grinding and tableting on physicochemical stability of an anticancer drug, TAT-59" Chemical and Pharmaceutical Bulletin, vol. 44, No. 10, 1996, pp. 1931-1934, XP002196671 Tokyo (JP)*p. 1932, col. 2, line 2—p. 1933, col. 1, line 1*.

* cited by examiner

*Primary Examiner*—Mark Rosenbaum
(74) *Attorney, Agent, or Firm*—Greenberg Traurig LLP; Eugene C. Rzucidlo

(57) ABSTRACT

The present invention has for its object to provide a method of micronizing (E)-4-[2-[2-[N-acetyl-N-(4-methoxybenzenesulfonyl)amino]phenylethenyl]pyridine 1-oxide while maintaining its crystalline.

The present invention relates to a method of micronizing the above compound characterized in that the compound is comminuted, for example, to the extent that the mean particle diameter of the compound will be 1~25 μm with 50 μm and larger particles accounting for 2% or less with a mill of the open-circuit pulverizing type.

2 Claims, 2 Drawing Sheets

METHOD FOR PULVERIZING TO FINE POWDER

TECHNICAL FIELD

The present invention relates to a method of micronizing (E)-4-[2-[2-[N-acetyl-N-(4-methoxybenzenesulfonyl) amino]phenyl]ethenyl]-pyridine 1-oxide (hereinafter referred to as the present compound) which is a known substance having high antitumoral activity.

The present compound as such and its usefulness referred to above are described in detail in, inter alia, PCT WO95/27699.

BACKGROUND ART

In order to improve the absorption, solubility, content uniformity and AUC (bioavailability), among others, of a sparingly soluble drug, it is generally considered desirable to micronize the drug. Actually, for providing sparingly soluble drugs in the tablet or the like pharmaceutical dosage form, they are micronized into fine powders on many occasions.

The pulverizing systems for such micronization can be roughly classified into an open-circuit pulverizing system and a closed-circuit pulverizing system. The open-circuit pulverizing system comprises passing a pulverization load a few times within one minute or substantially only once through a pulverizing zone and the closed-circuit pulverizing system comprises passing a pulverization load many a time during a comparatively long time through a pulverizing zone.

Meanwhile, drugs in general may usually remain in a thermodynamically stable state in a crystalline form than in a non-crystalline form and, therefore, in consideration of the stability of the drug, the pulverizate of the drug is preferably provided in a crystalline form barring special circumstances.

DISCLOSURE OF INVENTION

The present invention has for its object to provide a method of micronizing the present compound while maintaining its crystalline form and a finely-divided pulverizate of the present compound.

After intensive research the inventors of the present invention found that the above object can be accomplished by micronizing the present compound with a mill of the open-circuit pulverizing type and have accordingly developed the present invention.

The present invention, therefore, is directed to a method of micronizing the present compound characterized in that the present compound is comminuted with a mill of the open-circuit pulverizing type.

The mill of said open-circuit pulverizing type which can be used in the present invention includes but is not limited to a high-speed rotary impact mill and a pneumatic mill.

Micronization of the present compound should be carried out to the extent that the mean particle diameter of the pulverizate will be 1~25 $\mu$m with 50 $\mu$m and larger particles accounting for 2% or less, preferably to the extent that all particles fall within the diameter range of 5~20 $\mu$m and particles not less than 50 $\mu$m in diameter account for 1% or less or even 0%. Accordingly, the crystalline form of the present compound (hereinafter referred to as the present pulverizate) with a mean particle diameter of 1~25 $\mu$m with 50 $\mu$m and larger particles constituting a fraction of not more than 2%, preferably with a mean particle diameter of 5~20 $\mu$m with 50 $\mu$m and larger particles constituting a fraction of not more than 1% or 0%, is also subsumed in the scope of the present invention.

When a high-speed rotary impact mill is used, the pulverization is preferably carried out at a rotational speed of not less than 10,000 rpm, particularly not less than 20,000 rpm, although the optimum pulverizing condition depends on the type of machine and the drug lot, among other variables. When a pneumatic mill is used, the pulverization is preferably carried out at an air supply rate of 0.5~50 m$^3$/min and a pressure of 3~7 kg/cm$^2$, particularly an air supply rate of 10~45 m$^3$/min and a pressure of 5~6 kg/cm$^2$.

The micronization according to the invention can be easily accomplished by feeding the present compound to a mill of the open-circuit pulverizing type at a suitable rate (e.g. 10 g~1,000 kg/hr) for micronization.

The present pulverizate can be used as a medicine in the same manner as the present compound, and a pharmaceutical composition comprising the present pulverizate as an active ingredient can be used as an anticaner drug in cancer of the lung, cancer of the mammary gland, cancer of the digestive tract, cancer of the prostate, and cancer of the blood, among other diseases.

The pharmaceutical composition (hereinafter referred to as the present composition) comprising the present pulverizate as an active ingredient can be manufactured by using the present pulverizate as it is alone or together with a pharmaceutically acceptable, nontoxic and inert carrier according to a formulation including 0.1%~99.5%, preferably 0.5%~90%, of the pulverizate and can be administered to animals inclusive of man.

As said carrier, a solid, semisolid or liquid diluent, a filler, and one or more other formulation additives can be employed. The present composition is preferably administered in a unit dosage form. The present composition can be administered orally, parenterally, locally (transdermal delivery, instillation into the eye or pernasal delivery), or rectally, with the oral route being particularly preferred. Of course, a dosage form suited to the selected route of administration is employed.

The dosage of the present pulverizate for use as a medicine should be judiciously established in consideration of patient factors, e.g. age and body weight, the route of administration, the nature and severity of illness, indication and so on. Usually, however, the range of 1 mg~500 mg/day, preferably 2.5 mg~200 mg/day is appropriate for an adult human. Lower doses may be sufficient in some cases, while higher doses may be necessary in others. The above dosage can be administered in 2~4 divided doses a day.

BEST MODE FOR CARRYING OUT THE INVENTION

The following examples, comparative example, and test examples illustrate the present invention in further detail.

EXAMPLE 1

The bulc powder, 50 g, of the present compound (mean particle diameter 25.9 $\mu$m) was fed to a pin mill (Stud Mill 63C, Hosokawa Micron K.K.), a high-speed rotary impact mill of the open-circuit pulverizing type, by means of a load feeder screw at a rate of 100 g/hr and pulverized with a power supply of 200 V at a rotational speed of 20,000 rpm, and the pulverizate (the present pulverizate), 44.2 g, was recovered in a recovery bottle.

EXAMPLE 2

The bulc powder, 230 g, of the present compound (mean particle diameter 24.2 μm) was fed to a hammer mill (Sample Mill AP-S, Hosokawa Micron K.K.), a high-speed rotary impact mill of the open-circuit pulverizing type, by means of a load feeder screw at a rate of 100 g/hr and pulverized with a power supply of 200 V at a rotational speed of 11,700 rpm, and the pulverizate (the present pulverizate), 205.9 g, was recovered in a recovery bottle.

COMPARATIVE EXAMPLE 1

The bulc powder of the present compound (2 g; mean particle diameter 25.9 μm) was placed in the bowl (25 ml agate bowl, effective capacity 10 ml, number of balls 10, ball diameter 12 mm) of a planetary ball-mill (P-7, Fritsch Japan K.K.), a mill of the closed-circuit pulverizing type, and pulverized at 2,480 rpm for 2 hours to give 1.4 g of a pulverizate. In the course, the pulverizate was withdrawn at 30 minutes and 60 minutes of pulverization, ground in an agate mortar and about 0.2 g each of the resulting powders was taken as a sample.

TEST EXAMPLE 1

Determination of Particle Diameter

Twenty (20) mg each of the pre-pulverized present compound and the pulverizates of the compound as obtained in Examples 1 and 2 and Comparative Example 1 was taken in a test tube and 5 ml of silicone oil (product of Shin-Etsu Chemical Co.) was added. The mixture was stirred with a bench-top mixer for 20 seconds and further dispersed with a bench-top supersonic washer (UT-51N, product of Sharp Corporation) for 5 minutes. Then, the particle size distribution was determined with an ultracentrifugal automatic particle size distribution analyzer (CAPA-700, manufactured by Horiba, Ltd.). The results are shown in Table 1.

TABLE 1

| | | Before pulverization | After pulverization |
|---|---|---|---|
| Example 1 | Mean | 25.9 ± 43.3 μm | 9.7 ± 4.3 μm |
| | ≧30 μm | 35.5% | 0% |
| | ≧50 μm | 20.4% | — |
| Example 2 | Mean | 24.2 ± 31.2 μm | 15.2 ± 6.8 μm |
| | ≧30 μm | 26.6% | 6.8% |
| | ≧50 μm | 12.8% | 0% |
| | Before pulverization | | |
| Comparative Example | Mean | 25.9 ± 43.3 μm | |
| | ≧30 μm | 35.5% | |
| | ≧50 μm | 20.4% | |
| | After pulverization | | |
| After 30 min. | Mean | 15.1 μm | |
| After 60 min. | Mean | 12.4 μm | |
| After 120 min. | Mean | 10.7 ± 4.5 μm | |
| | ≧30 μm | 0% | |
| | ≧50 μm | — | |

TEST EXAMPLE 2

Confirmation of Crystalline State

Using each of the unpulverized present compound and the pulverizates of the same compound as obtained in Examples 1 and 2 and Comparative Example 1, the powder X-ray diffraction pattern was recorded with a powder x-ray diffraction analyzer (RAD-2B, manufactured by Rigaku Denki). The results are shown in FIGS. 1~3.

It will be apparent from the drawings that the pulverizates as micronized with a mill of the open-circuit pulverizing type retained the crystalline form, showing X-ray diffraction peaks. On the other hand, the pulverizate prepared with a mill of the closed-circuit pulverizing type showed a disappearance of X-ray diffraction peaks with the progress of pulverization and had changed to a non-crystalline compound showing no X-ray diffraction peaks after a pulverization time of 60 minutes.

TEST EXAMPLE 3

Administration Experiment (in vivo)

A capsule prepared using the unpulverized present compound and a capsule prepared using the pulverizate obtained in Example 1 (the present pulverizate) according to the physical blending formula shown in Table 2 were respectively administered orally to 4 crab-eating monkeys (male, aged 6~9 years). The blood was serially sampled and the plasma concentration of the metabolite of the present compound [(E)-4-[2-[2-[N-(4-methoxybenzenesulfonyl)amino]phenyl]-ethenyl]pyridine 1-oxide] was determined by HPLC. The results are shown in FIG. 4.

TABLE 2

| (physical blending formula) | |
|---|---|
| The present pulverizate | 300 mg |
| Lactose | 103 mg |
| Starch | 44.5 mg |
| Avicel ® | 35 mg |
| Hydroxypropylcellulose SL | 15 mg |
| Magnesium stearate | 2.5 mg |
| Total | 500 mg |

It will be apparent from FIG. 2 that the plasma concentration of the present compound can be significantly increased by micronizing the compound.

Figure 1:
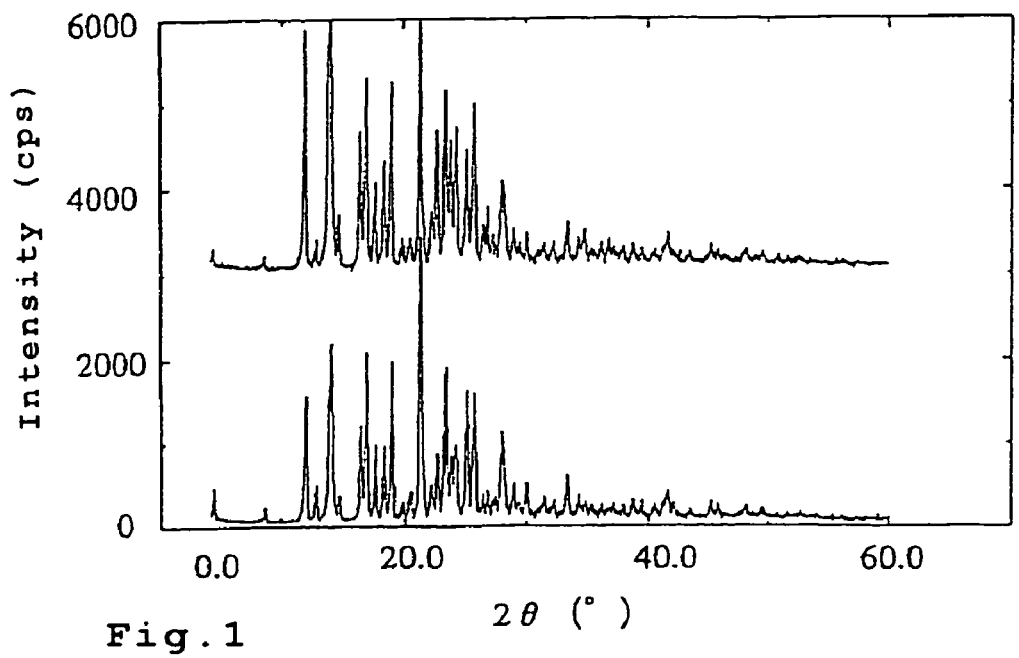
FIG. 1 shows X-ray diffraction patterns relevant to Example 1. In the figure, the top row shows the X-ray diffraction pattern after pulverization and the bottom row shows the X-ray diffraction pattern before pulverization. The abscissa represents the diffraction angle (°) and the ordinate represents the intensity (cps).
Figure 2:
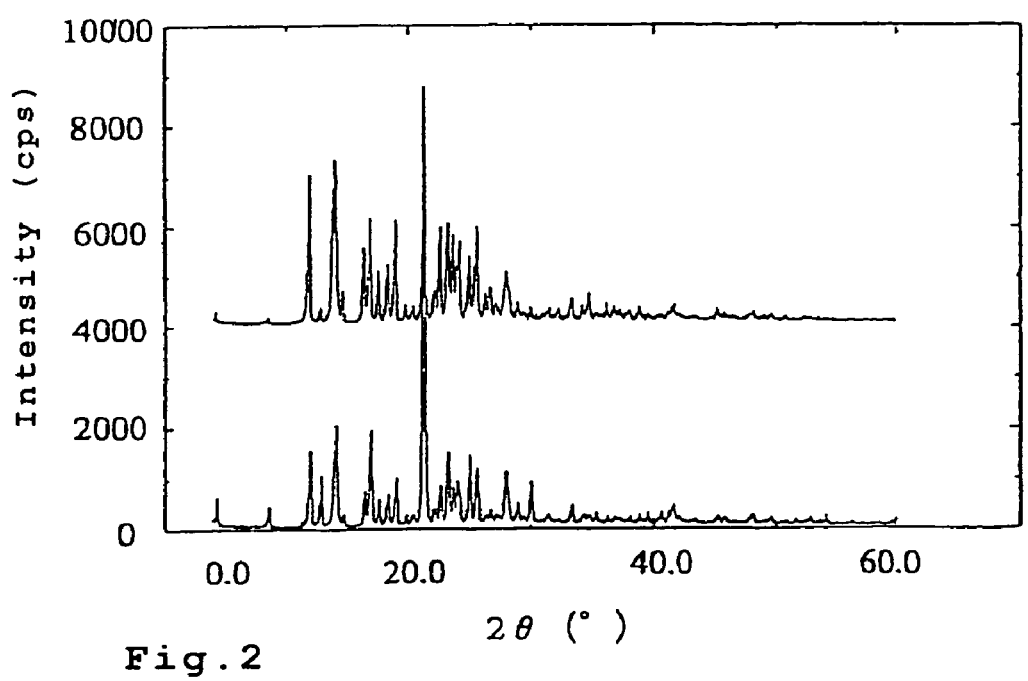
FIG. 2 shows X-ray diffraction patterns relevant to Example 2. In the figure, the top row shows the X-ray diffraction pattern after pulverization and the bottom row shows the X-ray diffraction pattern before pulverization. The abscissa represents the diffraction angle (°) and the ordinate represents the intensity (cps).
Figure 3:
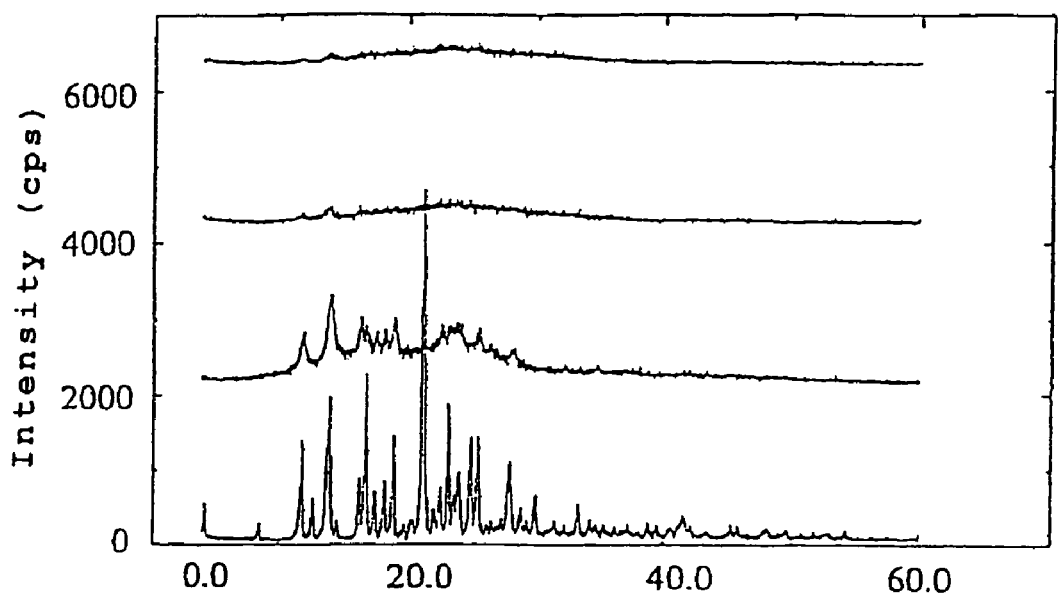
FIG. 3 shows X-ray diffraction patterns relevant to Comparative Example 1. In the figure, the lowermost row shows the X-ray diffraction pattern before pulverization, the second lower row shows the X-ray diffraction pattern after 30 minutes of pulverization, the second upper row shows the X-ray diffraction pattern after 60 minutes of pulverization, and the uppermost row shows the X-ray diffraction pattern after 120 minutes of pulverization. The abscissa represents the diffraction angle (°) and the ordinate represents the intensity (cps).
Figure 4:
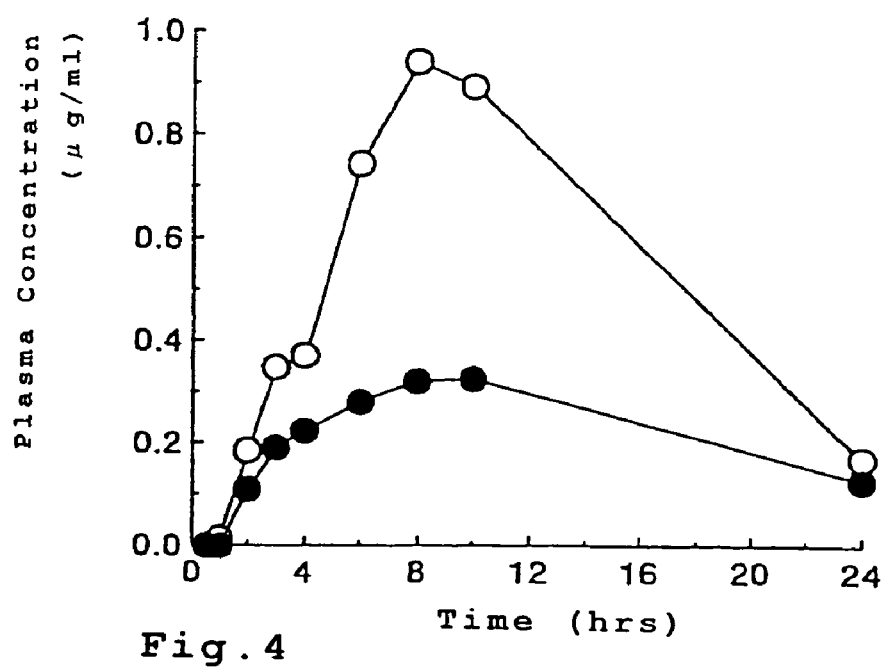
FIG. 4 shows the plasma concentration time course of the metabolite of the present compound. -○- represents the result for the present compound micronized in accordance with the invention (the present pulverizate) and -●- represents the results for the present compound prior to micronization. The abscissa represents time (hrs) and the ordinate represents the plasma concentration (μg/ml) of the metabolite.

What is claimed is:

1. A method for producing a plurality of crystalline (E)-4-[2-[2-[N-acetyl-N-(4-methoxybenzenesulfonyl)amino]phenyl]-ethenyl]pyridine 1-oxide particles with a mean particle diameter of from 1 μm to about 25 μm with particles larger than 50 μm constituting a fraction of not more than 2% of a total number of particles, comprising the step of micronizing the crystalline compound with an open-circuit pulverizing type mill and obtaining a pulverizate in which the crystallinity of the compound is retained.

2. The production method of claim 1 wherein said open-circuit pulverizing type mill is either a high-speed rotary impact mill or a pneumatic mill.

* * * * *